United States Patent
Arenson et al.

(10) Patent No.: US 6,850,588 B2
(45) Date of Patent: Feb. 1, 2005

(54) RADIATION EXPOSURE LIMITING SCHEME

(75) Inventors: Jerome Stephen Arenson, Haifa (IL); Haim E. Gelman, Migdal Haemek (IL); David Ruimi, Netania (IL)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 75 days.

(21) Appl. No.: 10/064,541

(22) Filed: Jul. 25, 2002

(65) Prior Publication Data

US 2004/0017890 A1 Jan. 29, 2004

(51) Int. Cl.$^7$ .............................................. H05G 1/60
(52) U.S. Cl. .......................... 378/16; 378/108; 378/110; 378/112; 378/117
(58) Field of Search ............................. 378/8, 16, 95, 378/108, 109, 110, 111, 112, 117; 600/407, 425

(56) References Cited

U.S. PATENT DOCUMENTS

| | | | | |
|---|---|---|---|---|
| 5,379,333 A | * | 1/1995 | Toth | 378/16 |
| 5,400,378 A | * | 3/1995 | Toth | 378/16 |
| 5,450,462 A | * | 9/1995 | Toth et al. | 378/16 |
| 5,457,724 A | * | 10/1995 | Toth | 378/4 |
| 5,485,494 A | * | 1/1996 | Williams et al. | 378/16 |
| 5,661,773 A | * | 8/1997 | Swerdloff et al. | 378/65 |
| 5,696,807 A | * | 12/1997 | Hsieh | 378/109 |
| 5,822,393 A | * | 10/1998 | Popescu | 378/108 |
| 5,867,555 A | * | 2/1999 | Popescu et al. | 378/16 |
| 5,873,826 A |  | 2/1999 | Gono et al. | 600/425 |
| 6,067,341 A | * | 5/2000 | Horiuchi | 378/8 |
| 6,094,468 A | * | 7/2000 | Wilting et al. | 378/8 |
| 6,385,280 B1 | * | 5/2002 | Bittl et al. | 378/16 |
| 6,435,717 B1 | * | 8/2002 | Kohler et al. | 378/206 |
| 6,487,431 B1 | * | 11/2002 | Iwano et al. | 600/407 |
| 6,501,820 B2 | * | 12/2002 | Guendel | 378/15 |
| 2001/0019599 A1 |  | 9/2001 | Guendel | 378/15 |
| 2003/0043956 A1 |  | 3/2003 | Cherek et al. | 378/4 |

FOREIGN PATENT DOCUMENTS

| | | | |
|---|---|---|---|
| DE | 199 51 496 | 5/2000 | ............ A61B/19/00 |
| EP | 0 819 407 | 1/1998 | ............ A61B/6/10 |
| WO | WO 02/056771 A1 | 1/2001 | |
| WO | 02 056771 | 7/2002 | ............ A61B/6/10 |

OTHER PUBLICATIONS

Search Report for European Patent Application 03254497.5, dated Oct. 20, 2003, Search performed by the Hague, Examiner R. Visser on Oct. 9, 2003. 3 pages.

* cited by examiner

*Primary Examiner*—Allen C. Ho
(74) *Attorney, Agent, or Firm*—Cantor Colburn LLP

(57) ABSTRACT

A method and system for reducing radiation exposure from an imaging system including determining an entry location, operating the imaging system so as to cause the imaging system to emit radiation having a radiation intensity, controlling the radiation intensity in a manner responsive to the entry location so as to create image data and processing the image data so as to create processed image data. In an alternative embodiment, a medium encoded with a machine-readable computer program code for reducing radiation exposure from an imaging system, the medium including instructions for causing a controller to implement the aforementioned method.

19 Claims, 4 Drawing Sheets

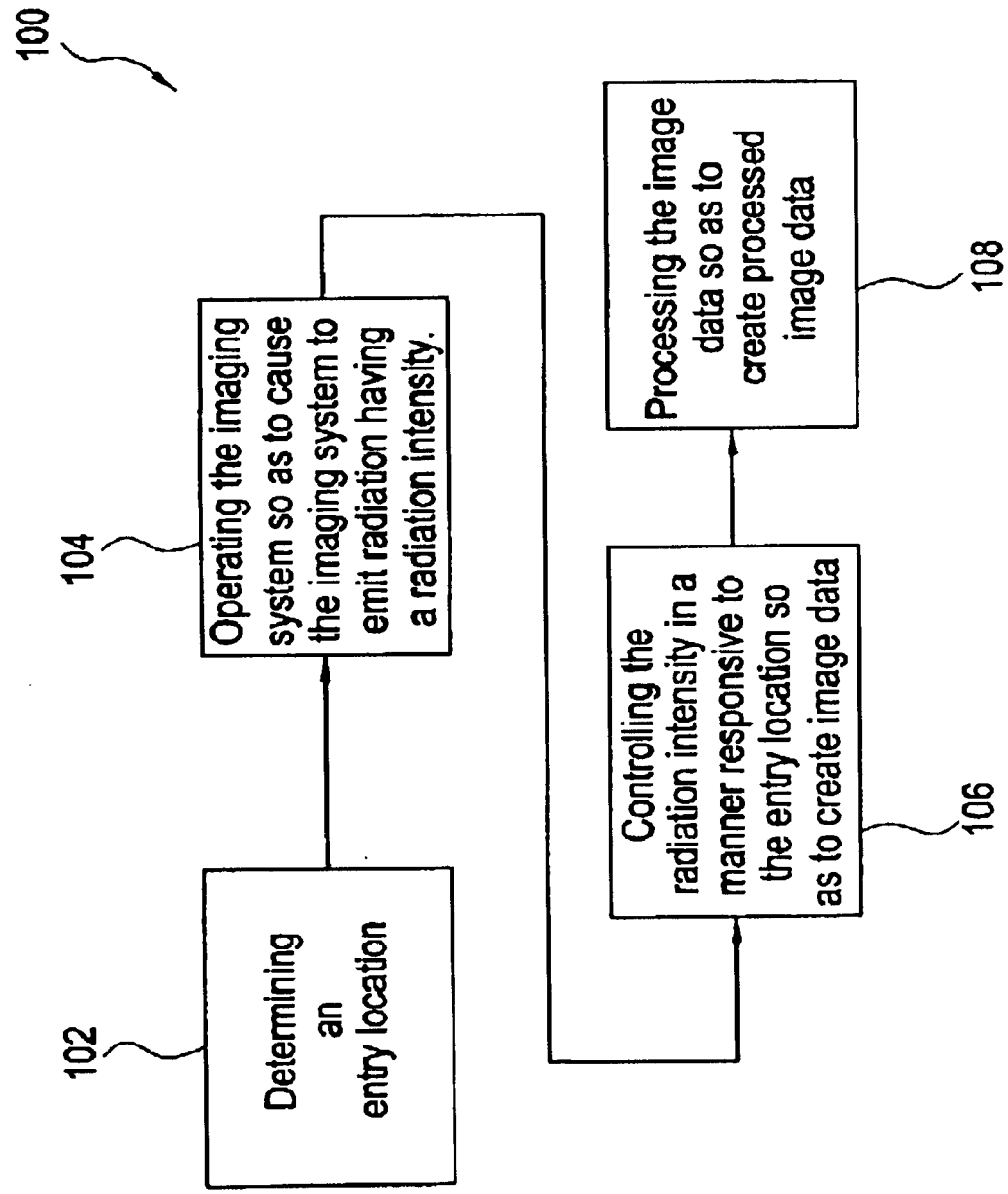

ial sample that
may be used for analysis.

RADIATION EXPOSURE LIMITING SCHEME

BACKGROUND OF INVENTION

This invention relates generally to a radiation exposure limiting scheme and more particularly to a radiation exposure limiting scheme for reducing the radiation exposure of a physician during the operation of an imaging system.

In at least one known computed tomography (CT) imaging system configuration, an x-ray source projects a fan-shaped, or a cone-shaped, beam which is collimated to lie within an X-Y-Z volume of a Cartesian coordinate system, wherein the X-Y-Z volume is generally referred to as an "imaging volume" and usually includes a set of X-Y planes generally referred to as the "imaging planes". An array of radiation detectors, wherein each radiation detector includes a detector element, are disposed within the CT system so as to received this beam. An object, such as a patient, is disposed within the imaging plane so as to be subjected to the x-ray beam wherein the x-ray beam passes through the object. As the x-ray beam passes through the object being imaged, the x-ray beam becomes attenuated before impinging upon the array of radiation detectors. The intensity of the attenuated beam radiation received at the detector array is responsive to the attenuation of the x-ray beam by the object, wherein each detector element produces a separate electrical signal responsive to the beam attenuation at the detector element location. These electrical signals are referred to as x-ray attenuation measurements.

In addition, the x-ray source and the detector array may be rotated, with a gantry within the imaging volume, around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and the detector array. In an axial scan, the projection data is processed so as to construct an image that corresponds to two-dimensional slices taken through the object.

One method for reconstructing an image from a set of projection data is referred to as the "filtered back-projection technique". This process converts the attenuation measurements from a scan into discrete integers, ranging from −1024 to +3072, called "CT numbers" or "Hounsfield Units" (HU). These HU's are used to control the brightness of a corresponding pixel on a cathode ray tube or a computer screen display in a manner responsive to the attenuation measurements. For example, an attenuation measurement for air may convert into an integer value of −1000HU's (corresponding to a dark pixel) and an attenuation measurement for very dense bone matter may convert into an integer value of +3000 (corresponding to a bright pixel), whereas an attenuation measurement for water may convert into an integer value of 0HU's (corresponding to a gray pixel). This integer conversion, or "scoring" allows a physician or a technician to determine the density of matter based on the intensity of the computer display.

Once a suspicious mass, such as a tumor, cyst and/or lesion, is discovered an interventional procedure, such as a needle biopsy or a needle aspiration, is usually performed to obtain tissue samples needed to determine whether the mass is cancerous or benign. To do this, a needle controlled by a physician is guided to the mass using simultaneous images, such as fluoro images, produced by the imaging system. This allows a physician to manipulate the needle tip towards the suspected tumor tissue so as to obtain a tissue sample that may be used for analysis.

However, although an interventional procedure using an imaging system is an excellent diagnostic and evaluation tool, each time an interventional procedure is performed by a physician, the physician's hand is exposed to radiation emitted from the imaging system. As such, if a physician performs a large number of interventional procedures over time, the cumulative radiation dose exposure to the physician's hand over time may become quite large. Given that health problems are known to be related to increasing exposure to radiation there is concern within the medical community that physicians performing these procedures may be over exposed to imaging system radiation.

One method to address the problem of physician radiation dose exposure includes minimizing the emitter current of the imaging system and using special forceps to keep the physician's hands out of the radiation beam. Unfortunately, forceps have not been well received by the medical community because they restrict the tactile sensitivity and thus limits the delicate physician control required for interventional procedures. Moreover, it has been found that minimizing the emitter current of the imaging system during an interventional procedure while still providing sufficient radiation for qualitative image generation still results in a significant cumulative radiation dose to the physician repeatedly performing the interventional procedures. As such, these methods are not well suited for repeated interventional procedures.

The above discussed and other features and advantages of the present invention will be appreciated and understood by those skilled in the art from the following detailed description and drawings.

SUMMARY OF INVENTION

The above discussed and other drawbacks and deficiencies are overcome or alleviated by a method for reducing radiation exposure from an imaging system comprising: determining an entry location; operating the imaging system so as to cause the imaging system to emit radiation having a radiation intensity; controlling the radiation intensity in a manner responsive to the entry location so as to create image data; and processing the image data so as to create processed image data.

In an alternative embodiment, a medium encoded with a machine-readable computer program code for reducing radiation exposure from an imaging system, the medium including instructions for causing a controller to implement the aforementioned method.

In another alternative embodiment, a method for reducing radiation exposure from an imaging system comprising: obtaining an object to be scanned; operating the imaging system so as to create image data; displaying the image data on an output device; and processing the image data using a processing device, wherein the processing device, determines an entry location; operates the imaging system so as to cause the imaging system to emit radiation having a radiation intensity; controls the radiation intensity in a manner responsive to the entry location so as to create image data; and processes the image data so as to create processed image data.

In another alternative embodiment, a system for reducing radiation exposure from an imaging system comprising: a gantry having an x-ray source and a radiation detector array, wherein the gantry defines a patient cavity and wherein the x-ray source and the radiation detector array are rotatingly associated with the gantry so as to be separated by the patient cavity; a patient support structure movingly associated with the gantry so as to allow communication with the patient cavity; and a processing device, wherein the processing device, determines an entry location; operates the imaging system so as to cause the imaging system to emit radiation having a radiation intensity; controls the radiation intensity in a manner responsive to the entry location so as to create image data; and processes the image data so as to create processed image data.

In another alternative embodiment, a system for reducing radiation exposure from an imaging system comprising: an imaging system; a patient support structure movingly associated with the imaging system so as to allow communication between the imaging system and a patient, wherein the imaging system generates image data responsive to the patient; and a processing device, wherein the processing device, determines an entry location; operates the imaging system so as to cause the imaging system to emit radiation having a radiation intensity; controls the radiation intensity in a manner responsive to the entry location so as to create image data; and processes the image data so as to create processed image data.

The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures:

FIG. 3 is a block diagram describing a method for reducing radiation exposure from an imaging system;

DETAILED DESCRIPTION

Figure 1:
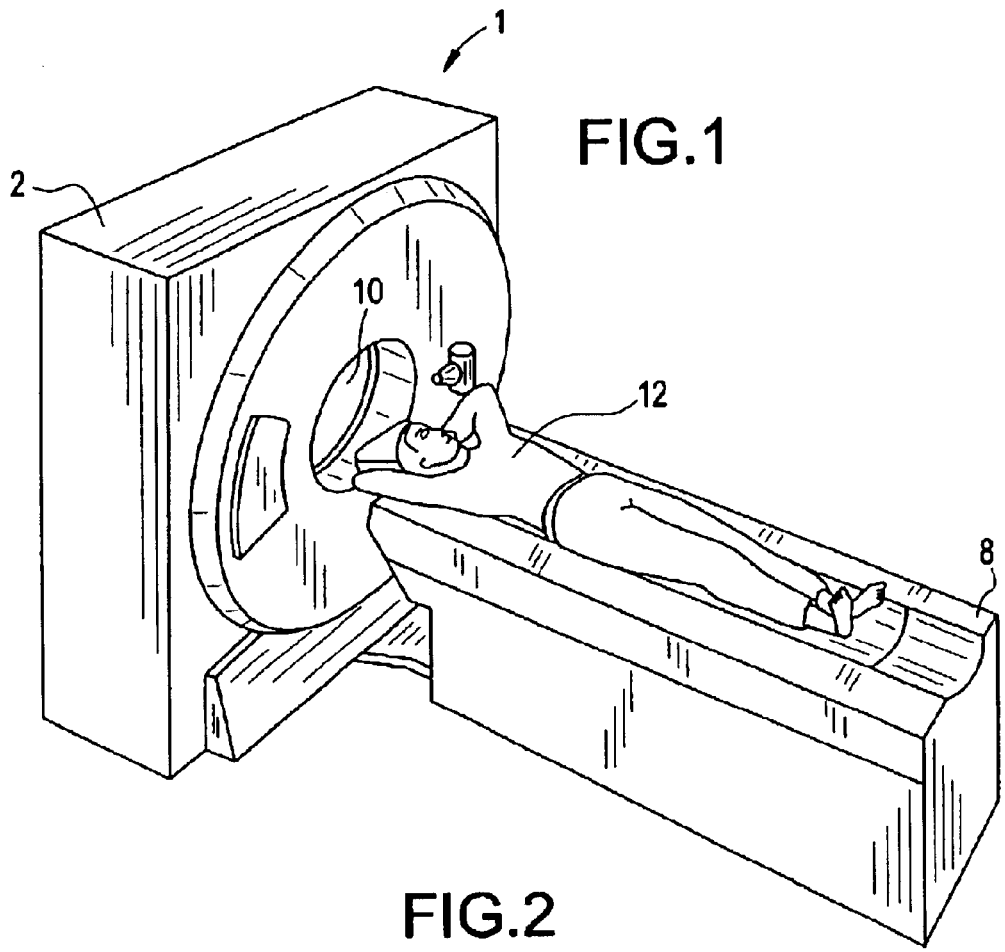
FIG. 1 is a perspective view of a CT imaging system and a patient disposed for imaging.
Figure 2:
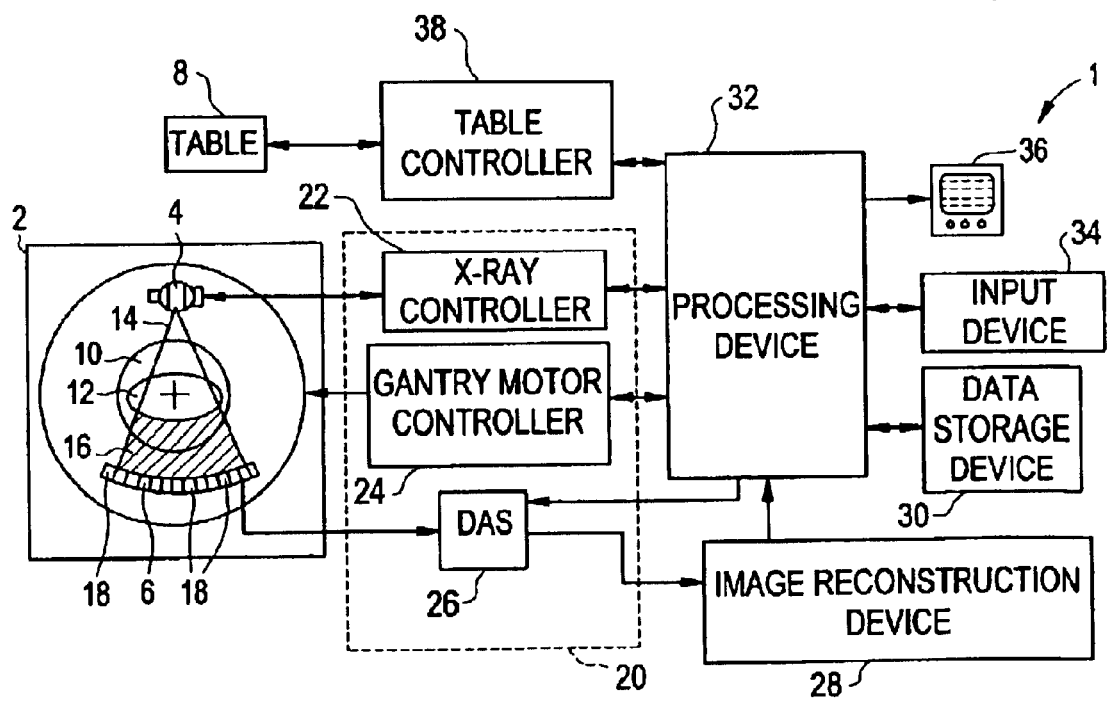
FIG. 2 is a block schematic diagram of a CT imaging system.

Referring to FIG. 1 and FIG. 2 a representative CT imaging system 1 is shown and preferably includes a gantry 2 having an x-ray source 4, a radiation detector array 6, a patient support structure 8 and a patient cavity 10, wherein x-ray source 4 and radiation detector array 6 are opposingly disposed so as to be separated by patient cavity 10. A patient 12 is preferably disposed upon patient support structure 8 which is then disposed within patient cavity 10. X-ray source 4 projects an x-ray beam 14 toward radiation detector array 6 so as to pass through patient 12. X-ray beam 14 is preferably collimated by a collimate (not shown) so as to lie within an X-Y-Z volume a Cartesian coordinate system referred to as an "imaging volume". After passing through and becoming attenuated by patient 12, attenuated x-ray beam 16 is preferably received by radiation detector array 6. Radiation detector array 6 preferably includes a plurality of detector elements 18 wherein each of the detector elements 18 receives attenuated x-ray beam 16 and produces an electrical signal responsive to the intensity of attenuated x-ray beam 16.

Although the embodiments described herein are described as applying to a computed tomography imaging system 1, it should be stated that the embodiments described herein may be applied to any imaging system suitable to the desired end purpose, such as an imaging system having a stationary ring and/or arc of detector arrays which surround the patient cavity, wherein the radiation source moves around patient 12 irradiating the detector elements within the stationary ring and/or arc.

In addition, x-ray source 4 and radiation detector array 6 are preferably rotatingly disposed relative to gantry 2 and patient support structure 8, so as to allow x-ray source 4 and radiation detector array 6 to rotate around patient support structure 8 when patient support structure 8 is disposed within patient cavity 10. X-ray projection data is obtained by rotating x-ray source 4 and radiation detector array 6 around patient 12 during a scan. X-ray source 4 and radiation detector array 6 are preferably communicated with a control mechanism 20 associated with CT imaging system 1. Control mechanism 20 preferably controls the rotation and operation of x-ray source 4 and/or radiation detector array 6.

Control mechanism 20 preferably includes an x-ray controller 22 communicated with x-ray source 4, a gantry motor controller 24, and a data acquisition system (DAS) 26 communicated with radiation detector array 6, wherein x-ray controller 22 provides power and timing signals to x-ray source 4, gantry motor controller 24 controls the rotational speed and angular position of x-ray source 4 and radiation detector array 6 and DAS 26 receives the electrical signal data produced by detector elements 18 and converts this data into digital signals for subsequent processing. CT imaging system 1 also preferably includes an image reconstruction device 28, a data storage device 30 and a processing device 32, wherein processing device 32 is communicated with image reconstruction device 28, gantry motor controller 24, x-ray controller 22, data storage device 30, an input device 34 and an output device 36. Moreover, CT imaging system 1 also preferably includes a table controller 38 communicated with processing device 32 and patient support structure 8, so as to control the position of patient support structure 8 relative to patient cavity 10.

In accordance with an exemplary embodiment, patient 12 is preferably disposed on patient support structure 8, which is then positioned by an operator via processing device 32 so as to be disposed within patient cavity 10. Gantry motor controller 24 is operated via processing device 32 so as to cause x-ray source 4 and radiation detector array 6 to rotate relative to patient 12. X-ray controller 22 is operated via processing device 32 so as to cause x-ray source 4 to emit and project a collimated x-ray beam 14 toward radiation detector array 6 and hence toward patient 12. X-ray beam 14 passes through patient 12 so as to create an attenuated x-ray beam 16, which is received by radiation detector array 6.

Detector elements 18 receive attenuated x-ray beam 16, produces electrical signal data responsive to the intensity of attenuated x-ray beam 16 and communicates this electrical signal data to DAS 26. DAS 26 then converts this electrical signal data to digital signals and communicates both the digital signals and the electrical signal data to image reconstruction device 28, which performs high-speed image reconstruction. This information is then communicated to processing device 32, which stores the image in data storage device 30 and displays the digital signal as an image via output device 36.

Referring to FIG. 3, a flow diagram describing a method for reducing radiation exposure 100 from an imaging system 1 is shown and discussed. In accordance with an exemplary embodiment, an entry location 40 is determined, as shown in step 102. During an interventional procedure an instrument, such as a needle, is guided by a physician's hand with the help of imaging system 1 and entry location 40 represents the location of the physician's hand which is disposed within patient cavity 10 and hence within a radiation field 42, wherein radiation field 42 includes an average radiation distribution 44 and an angular radiation distribution 46. In addition, entry location 40 may be disposed within a pre-determined entry angular range 50. Although, entry location 40 is preferably determined via an entry cursor and/or a target location cursor, wherein the entry cursor and/or target location cursor is communicated with processing device 32 via input device 34, entry location 40 may be determined and/or estimated using any information, method and/or device suitable to the desired end purpose, such as processing of data extracted from a Fluoro scan procedure. For example, an on-line assessment of the angular position of entry location 40 (& hence physician's hand) may be performed in a manner responsive to changes of the x-ray attenuation distribution during the intervention process and/or a manner responsive to the x-ray distribution determined during the primary non-fluoro scan and/or in a manner responsive to any other suitable means of detection, such as Ultrasound and/or optical.

Figure 4A:
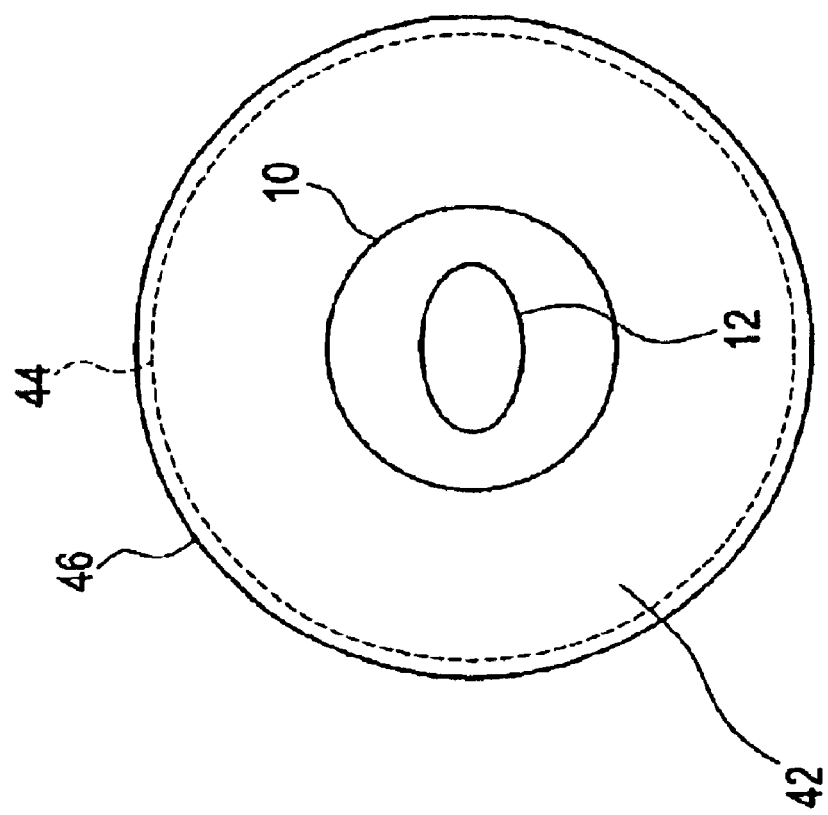
FIG. 4A is a distribution diagram showing the angular radiation distribution of an imaging system.

Referring to FIG. 4a, imaging system 1 is operated so as to cause x-ray source to emit radiation in the form of x-ray beam 14. As x-ray source 4 and radiation detector array 6 rotate around patient cavity 10 x-ray beam 14 creates radiation field 42 within patient cavity 10 wherein radiation field 42 includes average radiation distribution 44 and angular radiation distribution 46, as shown in step 104. As x-ray source 4 rotates around patient cavity 10 the gantry angular position or the angle at which x-ray beam 14 intersects patient 12, varies between 0° and 360°.

Figure 4B:
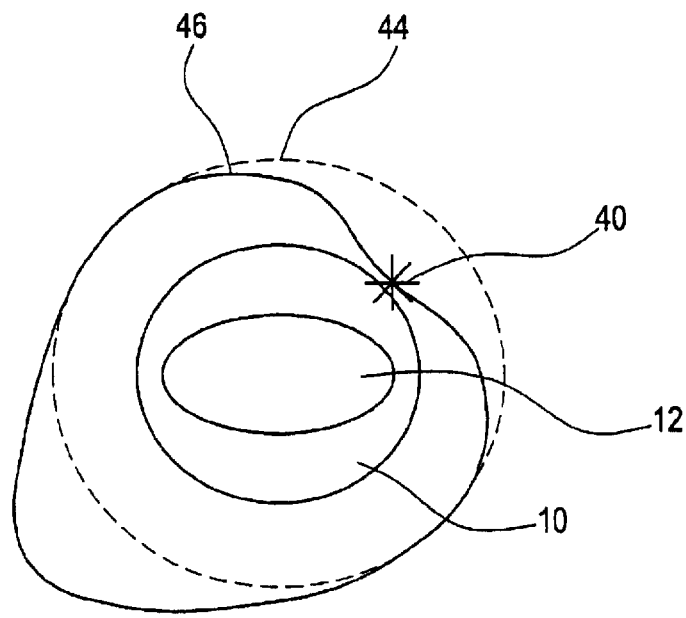
FIG. 4B is a distribution diagram showing the angular radiation distribution of an imaging system in accordance with an exemplary embodiment.
Figure 5:
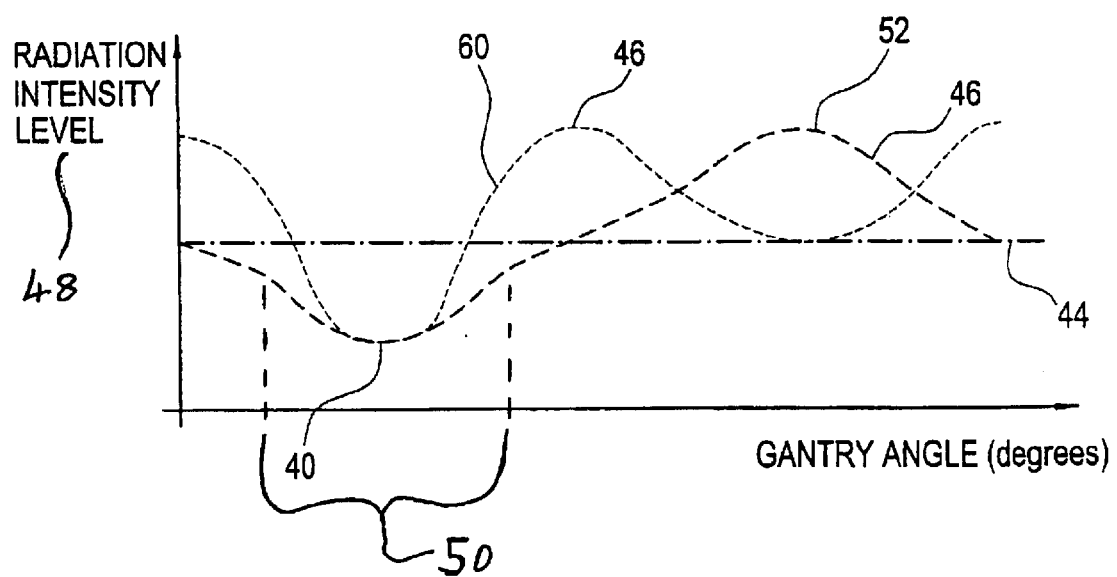
FIG. 5 is a graph of the radiation dose as a function of imaging system gantry angle in accordance with an exemplary embodiment.

Radiation intensity level 48 is then controlled in a manner responsive to entry location 40 and/or entry angular range 50 so as to create image data, as shown in step 106. Referring to FIG. 4B and FIG. 5, for a 360° image reconstruction 52 as the gantry angular position approaches entry location 40 and/or entry angular range 50, radiation intensity level 48 is decreased by a predetermined minimization amount so as to minimize the radiation intensity level 48 in the area of entry location 40. Similarly, as the gantry angular position approaches 180° from entry location 40 and/or entry angular range 50, radiation intensity level 48 is increased by a predetermined minimization amount so as to maximize the radiation intensity level 48 in the area of 180° from entry location 40. Predetermined minimization amount may be equal to the radiation intensity level so as to reduce the radiation intensity level at entry location 40 and/or within entry angular range 50 to be zero. Moreover, predetermined minimization amount may be any value suitable to the desired end purpose.

For a 180° image reconstruction 60, as the gantry angular position approaches entry location 40 and/or entry angular range 50, radiation intensity level 48 is decreased by a predetermined minimization amount so as to minimize the radiation intensity level 48 in the area of entry location 40. Similarly, as the gantry angular position approaches ±90° from entry location 40 and/or entry angular range 50, radiation intensity level 48 is increased by a predetermined minimization amount so as to maximize the radiation intensity level 48 in the area of ±90° from entry location 40 and/or entry angular range 50. This advantageously allows for a nearly constant average radiation distribution 44 through out the scan while allowing for the angular radiation distribution 46 to be modified. This advantageously allows the noise level of the image to be compensated by amplification of the emitter tube current at the opposing angle (180° for 360° recon) or the perpendicular angles (±90° for 180° recon). Moreover, the radiation exposure to the physician's hand will be dramatically reduced by the absorption of the patient's body (and, in most cases, by the patient table).

In addition, radiation intensity level 48 may be controlled by using a pre-determined radiation absorption angular profile (as measured during a previous rotation of the fluoroCT process and/or from a previously acquired static scan) as an input for additional modulation of x-ray beam 14 in order to significantly reduce patient radiation exposure dose. This pre-determined measure of radiation may be dependent upon the anatomy of patient 12 within the scan field. For example, if patient absorption at specific radiation source angles is low, as may be the case when x-ray source 4 is positioned anterior or posterior to the chest area of patient 12, then the radiation beam intensity may be significantly reduced at these angles without affecting image quality. Alternatively, when patient absorption is high, as may be the case for lateral radiation source angles, such as through the shoulder area or hip area of patient 12, x-ray source 4 may deliver a full un-modulated radiation exposure dose.

Another related feature includes using the angular current profile as an input for a weighting function in the reconstruction of the image. As the x-ray radiation is reduced the limited photon statistics give rise to increased image noise. Special noise reduction techniques and algorithms may be applied in the reconstruction process to reduce any image performance degradation. These algorithms may be controlled either by obtaining a measure of actual photon statistics during the acquisition process and/or by the priory knowledge of the angular current profile.

Furthermore, in order to eliminate streaks and other noise pattern artifacts, in the fluoro images, more than 180+fan degrees of data may be used for image reconstruction (e.g. 270 deg). The additional data beyond the last 180 degrees of scanning may be used to reduce image noise and streaks and significantly improve the image quality. The reduction in temporal resolution that this "over-scan" reconstruction entails may not be significant while using very fast rotation speed ($\leq 0.5$ sec) and a weighting function that includes only a small amount of "old" data.

Furthermore, in order to eliminate streaks and other noise pattern artifacts, in the final (static) image, more than 360 degrees of data may be used for image reconstruction (e.g. 540 deg). This implementation may occur following the 'dynamic' image reconstruction and display phase of FluoroCT imaging and may be used as a means of improving the quality of the final static image that remains on output device 36 after the real-time imaging has stopped. The additional data beyond the last 360 degrees of scanning may be used to reduce image noise and streaks and significantly improve the static image quality of this final image. The reduction in temporal resolution that this over-scan reconstruction entails may not be significant when viewing the static image at the completion of the FluoroCT procedure.

Referring to FIG. 6, the radiation intensity level 48 may also be controlled in a manner responsive to entry location 40 and/or entry angular range 50 so as to prevent radiation from being emitted from imaging system 1 while the gantry angular position approaches the entry location 40 and/or is within entry angular range 50. Radiation may be prevented from being emitted from imaging system 1 via any means suitable to the desired end purpose, such as by an electrical means (switch), a mechanical means (shutter) and/or an electro-mechanical means. This reduces and/or eliminates radiation exposure to a physician's hand while allowing the interventional procedure to continue. Moreover, direct radiation to the physician's hand will be eliminated while indirect radiation will be dramatically reduced by the absorption of the patient's body.

This image data is then processed so as to create processed image data, as shown in step 108. This advantageously allows for a significant dose reduction to the physician during interventional procedures using a FluoroCT scan while preserving patient dose and image quality.

This invention advantageously allows for interventional procedures to be performed while minimizing and/or eliminating radiation exposure to the performing physician. In addition, potential health problems may advantageously be avoided by reducing the physicians' exposure to x-ray radiation to more acceptable levels.

In accordance with an exemplary embodiment, a method for reducing radiation exposure from an imaging system 100 may be applied by any imaging system suitable to the desired end purpose, such as a magnetic resonance imaging (MRI), ultrasound, X-Ray, CT and/or PET.

In accordance with an exemplary embodiment, processing of FIG. 3 may be implemented through processing device 32 operating in response to a computer program. In order to perform the prescribed functions and desired processing, as well as the computations therefore (e.g., the execution of Fourier analysis algorithm(s), the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. It is also considered within the scope of the invention that the processing of FIG. 3 may be implemented by a controller located remotely from processing device 32.

As described above, the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) can be updated to implement the invention. The present invention can also be embodied in the form of computer program code, for example, whether stored in a storage medium, loaded into and/or executed by a computer, or transmitted over some transmission medium, such as electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for reducing radiation exposure from an imaging system adapted to provide a radiation distribution about an object cavity during a scan, the imaging system including an object cavity and a radiation source having a gantry angular position wherein the radiation source is rotatably associated with the imagine system so as to rotate around the object cavity, the method comprising:

determining an entry location representative of a location of a hand, the entry location having an entry angular range;

operating the imaging system so as to cause the imaging system to emit radiation having a radiation intensity and an angular radiation distribution comprising a first angular radiation distribution suitable for a 360 degree image reconstruction or a second angular radiation distribution suitable for a 180 degree image reconstruction, said first angular radiation distribution having a first average radiation distribution, said second angular radiation distribution having a second average radiation distribution, said first or second angular radiation distributions varying in intensity throughout the scan, and said first or second average radiation distributions being about constant throughout said scan;

controlling said radiation intensity in a manner responsive to said entry location so as to create image data; and processing said image data so as to create processed image data;

wherein said controlling comprises:

in response to said first radiation distribution, controlling said radiation intensity such that said radiation intensity is decreased relative to said first average radiation distribution by a predetermined minimization amount when said gantry angular position is within said entry angular range, and controlling said radiation intensity such that said radiation intensity is increased relative to said first average radiation distribution by the predetermined minimization amount when said gantry angular position is at about 180 degrees relative to said entry angular range; and in response to said second radiation distribution, controlling said radiation intensity such that said radiation intensity is decreased relative to said second average radiation distribution by a predetermined minimization amount when said gantry angular position is within said entry angular range, and controlling said radiation intensity such that said radiation intensity is increased relative to said second average radiation distribution by the predetermined minimization amount when said gantry angular position is at about 90 degrees relative to said entry angular range.

2. The method of claim 1, wherein said determining includes determining said entry location relative to said imaging system.

3. The method of claim 1, wherein said entry location is determined in a manner responsive to a FluoroCT scan.

4. The method of claim 1, wherein said operating includes operating the imaging system so as to cause said radiation source to rotate around said object cavity.

5. The method of claim 1, wherein said predetermined minimization amount is equal to said radiation intensity.

6. The method of claim 1, wherein said operating includes operating the imaging system so as to determine a radiation absorption angular profile, wherein said radiation absorption angular profile is responsive to said gantry angular position.

7. The method of claim 6, wherein said controlling includes controlling the imaging system so as to modulate said radiation intensity in a manner responsive to said radiation absorption angular profile.

8. A medium encoded with a machine-readable computer program code for reducing radiation exposure from an imaging system adapted to provide a radiation distribution about an object cavity during a scan, the imagine system including an object cavity and a radiation source having a gantry angular position wherein the radiation source is rotatably associated with the imaging system so as to rotate around the object cavity, said medium including instructions for causing a controller to implement a method comprising:

determining an entry location representative of a location of a hand, the entry location having an entry angular range;

operating the imaging system so as to cause the imaging system to emit radiation having a radiation intensity and an angular radiation distribution comprising a first angular radiation distribution suitable for a 360 degree image reconstruction or a second angular radiation distribution suitable for a 180 degree image reconstruction, said first angular radiation distribution having a first average radiation distribution, said second angular radiation distribution having a second average radiation distribution, said first or second angular radiation distributions varying in intensity throughout the scan, and said first or second average radiation distributions being about constant throughout said scan;

controlling said radiation intensity in a manner responsive to said entry location so as to create image data; and processing said image data so as to create processed image data;

wherein said controlling comprises:

in response to said first radiation distribution, controlling said radiation intensity such that said radiation intensity is decreased relative to said first average radiation distribution by a predetermined minimization amount when said gantry angular position is within said entry angular range, and controlling said radiation intensity such that said radiation intensity is increased relative to said first average radiation distribution by the predetermined minimization amount when said gantry angular position is at about 180 degrees relative to said entry angular range; and in response to said second radiation distribution, controlling said radiation intensity such that said radiation intensity is decreased relative to said second average radiation distribution by a predetermined minimization amount when said gantry angular position is within said entry angular range, and controlling said radiation intensity such that said radiation intensity is increased relative to said second average radiation distribution by the predetermined minimization amount when said gantry angular position is at about 90 degrees relative to said entry angular range.

9. The medium of claim 8, wherein said determining includes determining said entry location relative to said imaging system.

10. The medium of claim 8, wherein said entry location is determined in a manner responsive to a FluoroCT scan.

11. The medium of claim 17, wherein said operating includes operating the imaging system so as to cause said radiation source to rotate around said object cavity.

12. The medium of claim 8, wherein said predetermined minimization amount is equal to said radiation intensity.

13. The medium of claim 8, wherein said operating includes operating the imaging system so as to determine a radiation absorption angular profile, wherein said radiation absorption angular profile is responsive to said gantry angular position.

14. The medium of claim 13, wherein said controlling includes controlling the imaging system so as to modulate said radiation intensity in a manner responsive to said radiation absorption angular profile.

15. A method for reducing a physician's radiation exposure from an imaging system while maintaining patient dose and image quality, the imaging system including an object cavity and a radiation source having a gantry angular position wherein the radiation source is rotatably associated with the imaging system so as to rotate around the object cavity, the method comprising:

obtaining an object to be scanned;

operating the imaging system so as to create image data;

displaying said image data on an output device; and processing said image data using a processing device, wherein said processing device:

determines an entry location representative of a location of a physician's hand, the entry location having an entry angular range;

operates the imaging system so as to cause the imaging system to emit radiation having a radiation intensity and an angular radiation distribution comprising a first angular radiation distribution suitable for a 360 degree image reconstruction or a second angular radiation distribution suitable for a 180 degree image reconstruction, said first angular radiation distribution having a first average radiation distribution, said second angular radiation distribution having a second average radiation distribution, said first and or second angular radiation distributions varying in intensity throughout the scan, and said first or second average radiation distributions being about constant throughout a scan;

controls said radiation intensity in a manner responsive to said entry location so as to create image data; and processes said image data so as to create processed image data; wherein said processing device further:

in response to said first radiation distribution, controls said radiation intensity such that said radiation intensity is decreased relative to said first average radiation distribution by a predetermined minimization amount when said gantry angular position is within said entry angular range, and controls said radiation intensity such that said radiation intensity is increased relative to said first average radiation distribution by the predetermined minimization amount when said gantry angular position is at about 180 degrees relative to said entry angular range; and in response to said second radiation distribution, controls said radiation intensity such that said radiation intensity is decreased relative to said second average radiation distribution by a predetermined minimization amount when said gantry angular position is within said entry angular range, and controls said radiation intensity such that said radiation intensity is increased relative to said second average radiation distribution by the predetermined minimization amount when said gantry angular position is at about 90 degrees relative to said entry angular range.

16. A system for reducing the physician's radiation exposure from an imaging system while maintaining patient dose and image quality comprising:

a gantry having an x-ray source with a gantry angular position and a radiation detector array, wherein said gantry defines a patient cavity and wherein said x-ray source and said radiation detector array are rotatingly associated with said gantry so as to be separated by said patient cavity;

a patient support structure movingly associated with said gantry so as to allow communication with said patient cavity; and a processing device, wherein said processing device is adapted to:

determine an entry location representative of a location of a physician's hand, the entry location having an entry angular range;

operate the imaging system so as to cause the imaging system to emit radiation having a radiation intensity and an angular radiation distribution comprising a first angular radiation distribution suitable for a 360 degree image reconstruction or a second angular radiation distribution suitable for a 180 degree image reconstruction, said first angular radiation distribution having a first average radiation distribution, said second angular radiation distribution having a second average radiation distribution, said first or second angular radiation distributions varying in intensity throughout the scan, and said first or second average radiation distributions being about constant throughout a scan;

control said radiation intensity in a manner responsive to said entry location so as to create image data; and process said image data so as to create processed image data;

wherein said processing device is further adapted to:

in response to said first radiation distribution, control said radiation intensity such that said radiation intensity is decreased relative to said first average radiation distribution by a predetermined minimization amount when said gantry angular position is within said entry angular range, and control said radiation intensity such that said radiation intensity is increased relative to said first average radiation distribution by the predetermined minimization amount when said gantry angular position is at about 180 degrees relative to said entry angular range; and in response to said second radiation distribution, control said radiation intensity such that said radiation intensity is decreased relative to said second average radiation distribution by a predetermined minimization amount when said gantry angular position is within said entry angular range, and control said radiation intensity such that said radiation intensity is increased relative to said second average radiation distribution by the predetermined minimization amount when said gantry angular position is at about 90 degrees relative to said entry angular range.

17. The system of claim 16, wherein the imaging system is a computed tomography imaging system.

18. A system for reducing the physician's radiation exposure from an imaging system while maintaining patient dose and image quality comprising:

an imaging system including an object cavity and a radiation source having a gantry annular position wherein the radiation source is rotatably associated with the imaging system so as to rotate around the object cavity;

a patient support structure movingly associated with said imaging system so as to allow communication between said imaging system and a patient, wherein said imaging system generates image data responsive to said patient; and a processing device, wherein said processing device is adapted to:

determine an entry location representative of a location of a physician's hand, the entry location having an entry angular range;

operate the imaging system so as to cause the imaging system to emit radiation having a radiation intensity and an angular radiation distribution comprising a first angular radiation distribution suitable for a 360 degree image reconstruction or a second angular radiation distribution suitable for a 180 degree image reconstruction, said first angular radiation distribution having a first average radiation distribution, said second angular radiation distribution having a second average radiation distribution, said first or second angular radiation distributions varying in intensity throughout the scan, and said first or second average radiation distributions being about constant throughout a scan;

control said radiation intensity in a manner responsive to said entry location so as to create image data; and process said image data so as to create processed image data;

wherein said processing device is further adapted to:

in response to said first radiation distribution, control said radiation intensity such that said radiation intensity is decreased relative to said first average radiation distribution by a predetermined minimization amount when said gantry angular position is within said entry angular range, and control said radiation intensity such that said radiation intensity is increased relative to said first average radiation distribution by the predetermined minimization amount when said gantry angular position is at about 180 degrees relative to said entry angular range; and in response to said second radiation distribution, control said radiation intensity such that said radiation intensity is decreased relative to said second average radiation distribution by a predetermined minimization amount when said gantry angular position is within said entry angular range, and control said radiation intensity such that said radiation intensity is increased relative to said second average radiation distribution by the predetermined minimization amount when said gantry angular position is at about 90 degrees relative to said entry angular range.

19. The system of claim 18, wherein the imaging system is a computed tomography imaging system.

* * * * *